United States Patent [19]

Krämer et al.

[11] 4,264,772
[45] Apr. 28, 1981

[54] COMBATING FUNGI WITH 1-PHENYL-1-OXIMINO-2-(1,2,4-TRIAZOL-1-yl)-ETHANES

[75] Inventors: Wolfgang Krämer; Karl H. Büchel; Helmut Timmler, all of Wuppertal; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 22,913

[22] Filed: Mar. 22, 1979

[30] Foreign Application Priority Data

Apr. 18, 1978 [DE] Fed. Rep. of Germany ....... 2816817

[51] Int. Cl.$^3$ .................. A01N 43/64; C07D 249/08
[52] U.S. Cl. .................... 548/262; 542/416; 546/276; 548/101; 548/112; 424/232; 424/245; 424/269
[58] Field of Search ............ 542/413; 260/299, 308 R; 548/341, 262, 112; 424/269, 245; 546/276

[56] References Cited

U.S. PATENT DOCUMENTS 4,124,767 11/1978 Mixich et al. .................... 548/341

FOREIGN PATENT DOCUMENTS 2610022 9/1976 Fed. Rep. of Germany ...... 260/308 R
2723942 12/1978 Fed. Rep. of Germany ...... 260/308 R Primary Examiner—Alton D. Rollins
Attorney, Agent, or Firm—Sprung, Felfe, Horn, Lynch & Kramer

[57] ABSTRACT

A 1-phenyl,1-oximino-2-(1,2,4-triazol-1-yl)-ethane of the formula

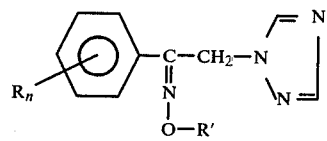

in which

R is halogen, alkyl, alkoxy, alkylthio, alkylsulphonyl, halogenoalkyl, nitro, cyano, optionally substituted phenyl or optionally substituted phenoxy, R' is alkyl, alkenyl, alkynyl, optionally substituted benzyl or optionally substituted styryl, and n is 0, 1, 2 or 3, or a salt thereof with a physiologically acceptable acid or a metal salt complex thereof which possesses fungicidal properties.

1 Claim, No Drawings

COMBATING FUNGI WITH 1-PHENYL-1-OXIMINO-2-(1,2,4-TRIAZOL-1-yl)-ETHANES

The present invention relates to and has for its objects the provision of particular new 1-phenyl-1-oximino-2-(1,2,4-triazol-1-yl)-ethanes which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that certain imidazolyl-oxime ethers and salts thereof, for example 1-(2,4-dichlorophenyl)-2-(imidazol-1-yl)-O-(2,4-dichlorobenzyl)-ethanone oxime-nitrate, have fungicidal properties (see DT-OS (German Published Specification ) No. 2,657,578). However, their action is not always satisfactory, especially when low amounts and concentrations are used.

The present invention now provides, as new compounds, the oximino-triazolyl-ethanes of the general formula

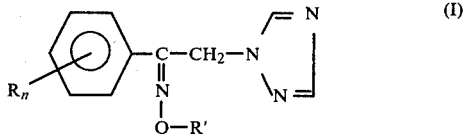

in which
R represents halogen, alkyl, alkoxy, alkylthio, alkylsulphonyl, halogenoalkyl, nitro, cyano, optionally substituted phenyl or optionally substituted phenoxy,
R' represents alkyl, alkenyl, alkynyl, optionally substituted benzyl or optionally substituted styryl and
n represents 0, 1, 2 or 3, the substituents R being selected independently of one another when n is 2 or more,
and their physiologically acceptable acid addition salts and metal salt complexes. They have powerful fungicidal properties.

Preferably, R represents halogen (especially fluorine, chlorine or bromine), nitro, cyano, alkyl with 1 to 4 carbon atoms, alkylsulphonyl with 1 to 4 carbon atoms, alkoxy with 1 or 2 carbon atoms, alkylthio with 1 or 2 carbon atoms, halogenoalkyl with up to 4 carbon atoms and up to 5 halogen atoms (especially with up to 2 carbon atoms and up to 3 identical or different halogen atoms, preferred halogen atoms being fluorine and chlorine, with trifluoromethyl being mentioned as a specific example of halogenoalkyl), or phenyl or phenoxy, either of which may optionally carry one or more substituents selected independently from halogen (especially fluorine, chlorine or bromine), cyano, nitro and halogenoalkyl with up to 2 carbon atoms and up to 3 identical or different halogen atoms (preferred halogen atoms being fluorine and chlorine and trifluoromethyl being mentioned as a specific example of halogenoalkyl), and R' represents alkyl, alkenyl or alkynyl with up to 4 carbon atoms in each case, or benzyl or styryl, either of which may optionally carry one or more substituents selected independently from halogen (especially fluorine, chlorine or bromine), cyano, nitro, amino, alkyl with 1 to 4 carbon atoms, phenyl, phenoxy and halogenoalkyl with up to 2 carbon atoms and up to 3 identical or different halogen atoms (preferred halogen atoms being fluorine and chlorine and trifluoromethyl being mentioned as a specific example of halogenoalkyl).

The compounds of the formula (I) can exist in the syn-form or anti-form; they are predominantly obtained as mixtures of the two forms.

Surprisingly, the oximino-triazolyl-ethanes according to the invention exhibit a considerably more powerful fungicidal activity, especially against species of powdery mildew and rust, than the imidazolyl-oxime ethers known from the state of the art, for example 1-(2,4-dichlorophenyl)-2-(imidazol-1-yl)-O-(2,4-dichlorobenzyl)-ethanone oxime, which are closely related substances chemically and from the point of view of their action. The active compounds according to the invention thus represent an enrichment of the art.

Particularly preferred oximino-triazolyl-ethanes of the formula (I) are those in which R represents chlorine, bromine, phenyl, chlorophenyl, bromophenyl, nitrophenyl, phenoxy, chlorophenoxy, bromophenoxy or nitrophenoxy, n represents the number 1 or 2 and R' represents methyl, ethyl, n-propyl, isopropyl, n-butyl, isobutyl, sec.-butyl, tert.-butyl, allyl, 2-methylallyl, propargyl, benzyl (which is optionally monosubstituted or disubstituted by chlorine, bromine, nitro, methyl, ethyl, phenyl or phenoxy) or styryl (which is optionally monosubstituted or disubstituted by chlorine).

The following compounds are specific examples which may be mentioned in addition to the compounds disclosed in the preparative examples: 1-(2,4-dichlorophenyl)-1-(allyloximino)-2-(1,2,4-triazol-1-yl)-ethane, 1-(2,4-dichlorophenyl)-1-(2,4-dichlorobenzyloximino)-2-(1,2,4-triazol-1-yl)-ethane, 1-(2,4-dichlorophenyl)-1-(propargyloximino)-2-(1,2,4-triazol-1-yl)-ethane, 1-(4-chlorophenyl)-1-(2,4-dichlorobenzyloximino)-2-(1,2,4-triazol-1-yl)-ethane, 1-(4-chlorophenyl)-1-(4-chlorobenzyloximino)-2-(1,2,4-triazol-1-yl)-ethane, 1-(2,4-dichlorophenyl)-1-(2,6-dichlorobenzyloximino)-2-(1,2,4-triazol-1-yl)-ethane, 1-(4-chlorophenyl)-1-(2,6-dichlorobenzyloximino)-2-(1,2,4-triazol-1-yl)-ethane, 1-(4-chlorophenyl)-1-(allyloximino)-2-(1,2,4-triazol-1-yl)-ethane, 1-(4-phenoxyphenyl)-1-(allyloximino)-2-(1,2,4-triazol-1-yl)-ethane, 1-(4,4'-chlorophenoxyphenyl)-1-(allyloximino)-2-(1,2,4-triazol-1-yl)-ethane, 1-(4,4'-chlorophenoxyphenyl)-1-(2,4-dichlorobenzyloximino)-2-(1,2,4-triazol-1-yl)-ethane, 1-(2,4-dichlorophenyl)-1-(4-nitrobenzyloximino)-2-(1,2,4-triazol-1-yl)-ethane, 1-(2,4-di-chlorophenyl)-1-(4-aminobenzyloximino)-2-(1,2,4-triazol-1-yl)-ethane, 1-(4-phenoxyphenyl)-1-(2,4-dichlorobenzyloximino)-2-(1,2,4-triazol-1-yl)-ethane, 1-(2,4-dichlorophenyl)-1-(methyloximino)-2-(1,2,4-triazol-1-yl)-ethane, 1-(4-bromophenyl)-1-(allyloximino)-2-(1,2,4-triazol-1-yl)-ethane, 1-(4,4'-chlorobiphenylyl)-1-(2,4-dichlorobenzyloximino)-2-(1,2,4-triazol-1-yl)-ethane, 1-(4-phenoxyphenyl)-1-(4-chlorobenzyloximino)-2-(1,2,4-triazol-1-yl)-ethane, 1-(4-phenoxyphenyl)-1-(2,6-dichlorobenzyloximino)-2-(1,2,4-triazol-1-yl)-ethane, 1-(4,4'-chlorophenoxyphenyl)-1-(methyloximino)-2-(1,2,4-triazol-1-yl)-ethane, 1-(4-phenoxyphenyl)-1-(propargyloximino)-2-(1,2,4-triazol-1-yl)-ethane, 1-(4-bromophenyl)-1-(2,4-dichlorobenzyloximino)-2-(1,2,4-triazol-1-yl)-ethane, 1-(4,4'-bromophenoxyphenyl)-1-(2,4-dichlorobenzyloximino)-2-(1,2,4-triazol-1-yl)-ethane, 1-(4,4'-bromophenoxyphenyl)-1-(allyloximino)-2-(1,2,4-triazol-1-yl)-ethane, 1-(4,4'-bromophenoxyphenyl)-1-(4-chlorobenzyloximino)-2-(1,2,4-triazol-1-yl)-ethane, 1-(2,4-dichlorophenyl)-1-(2-chlorobenzyloximino)-2-(1,2,4-triazol-1-yl)-ethane, 1-(2,4-dichlorophenyl)-1-(butyloximino)-2-(1,2,4-triazol-1-yl)-ethane, 1-(2,4-dichlorophenyl)-1-(3,4-dichlorobenzyloximino)-2-(1,2,4-triazol-1-yl)-ethane, 1-(2,4-dichlorophenyl)-1-(3-nitrobenzyloximino)-2-(1,2,4-triazol-1-yl)-ethane, 1-(4-bromophenyl)-1-(2,6-dichlorobenzyloximino)-2-(1,2,4-triazol-1-yl)-ethane, 1-(4,4'-bromophenoxyphenyl)-1-(3,6-dichlorobenzyloximino)-2-(1,2,4-triazol-1-yl)-ethane, 1-(4-bromophenyl)-1-(4-chlorobenzyloximino)-2-(1,2,4-triazol-1-yl)-ethane, 1-(4,4'-chlorobiphenylyl)-1-(2,6-dichlorobenzyloximino)-2-(1,2,4-triazol-1-yl)-ethane, 1-(2,4-dichlorophenyl)-1-(2-methylallyloximino)-2-(1,2,4-triazol-1-yl)-ethane, 1-(4,4'-chlorobiphenylyl)-1-(4-chlorobenzyloximino)-2-(1,2,4-triazol-1-yl)-ethane, 1-(4,4'-chlorophenoxyphenyl)-1-(4-chlorobenzyloximino)-2-(1,2,4-triazol-1-yl)-ethane, 1-(4,4'-chlorophenoxyphenyl)-1-(2,6-dichlorobenzyloximino)-2-(1,2,4-triazol-1-yl)-ethane, 1-(4,4'-chlorophenoxyphenyl)-1-(2-methylallyloximino)-2-(1,2,4-triazol-1-yl)-ethane, 1-(4,4'-chlorophenoxyphenyl)-1-(propargyloximino)-2-(1,2,4-triazol-1-yl)-ethane, 1-(4,4'-chlorophenoxyphenyl)-1-(2-chlorobenzyloximino)-2-(1,2,4-triazol-1-yl)-ethane, 1-(4,4'-chlorophenoxyphenyl)-1-(3,4-dichlorobenzyloximino)-2-(1,2,4-triazol-1-yl)-ethane, 1-(4,4'-chlorophenoxyphenyl)-1-(3-nitrobenzyloximino)-2-(1,2,4-triazol-1-yl)-ethane, 1-(4,4'-nitrophenoxyphenyl)-1-(allyloximino)-2-(1,2,4-triazol-1-yl)-ethane, 1-(2,4-dichlorophenyl)-1-(4-methylbenzyloximino)-2-(1,2,4-triazol-1-yl)-ethane, 1-(2,4-dichlorophenyl)-1-(3-phenoxybenzyloximino)-2-(1,2,4-triazol-1-yl)-ethane, 1-(4,4'-chlorophenoxyphenyl)-1-(3-phenoxybenzyloximino)-2-(1,2,4-triazol-1-yl)-ethane, 1-(4,4'-chlorophenoxyphenyl)-1-(4-methylbenzylamino)-2-(1,2,4-triazol-1-yl)-ethane, 1-(2,4-dichlorophenyl)-1-(styryloximino)-2-(1,2,4-triazol-1-yl)-ethane, 1-(4-biphenylyl)-1-(styryloximino)-2-(1,2,4-triazol-1-yl)-ethane, 1-(4,4'-chlorobiphenylyl)-1-(styryloximino)-2-(1,2,4-triazol-1-yl)-ethane, 1-(4-phenoxyphenyl)-1-(styryloximino)-2-(1,2,4-triazol-1-yl)-ethane, 1-(4,4'-chlorophenoxyphenyl)-1-(styryloximino)-2-(1,2,4-triazol-1-yl)-ethane, 1-(2,4-dichlorophenyl)-1-(2,4-dichlorostyryloximino)-2-(1,2,4-triazol-1-yl)-ethane, 1-(4,4'-chlorobiphenylyl)-1-(2,4-di-chlorostyryloximino)-2-(1,2,4-triazol-1-yl)-ethane, 1-(4,4'-chlorophenoxyphenyl)-1-(2,4-dichlorostyryloximino)-2-(1,2,4-triazol-1-yl)-ethane, 1-(3,4-dichlorophenyl)-1-(2,4-dichlorobenzyloximino)-2-(1,2,4-triazol-1-yl)-ethane, 1-(3,4-dichlorophenyl)-1-(butoximino)-2-(1,2,4-triazol-1-yl)-ethane and 1-(3,4-dichlorophenyl)-1-(allyloximino)-2-(1,2,4-triazol-1-yl)-ethane.

The invention also provides a process for the preparation of an oximino-triazolyl-ethane of the formula (I) in which a salt of an oxime, of the general formula

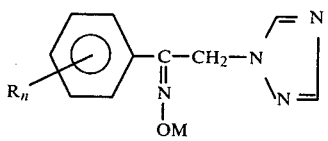

in which

R and $\underline{n}$ have the meanings stated above and
M represents an alkali metal or a quaternary ammonium or phosphonium group,
is reacted with a halide of the general formula $$R'—Hal \qquad (III),$$

in which

R' has the meaning stated above and
Hal represents chlorine or bromine, in the presence of a diluent.

Furthermore, the oximino-triazolyl-ethanes of the formula (I) can be converted into salts by reaction with acids, or the corresponding metal complexes can be obtained by reaction with metal salts.

If, for example, the sodium alkanolate of 1-(2,4-dichlorophenyl)-1-oxoimino-2-(1,2,4-triazol-1-yl)-ethane and 4-chlorobenzyl chloride are used as starting materials, the course of the reaction can be represented by the equation which follows:

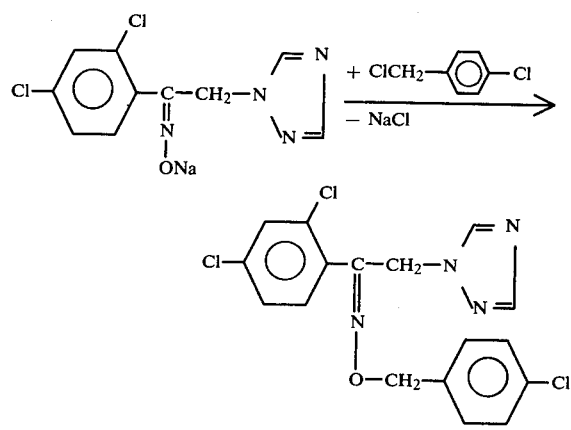

The oximino-ethylates to be used as starting materials are defined by the general formula (II). In this formula, M preferably represents lithium, sodium, potassium, tetrabutylammonium, N-benzyl-N,N,N-trimethylammonium, hexadecyltrimethylammonium, 2-hydroxyethyl-trimethylammonium, tetraethylammonium, tetramethylammonium, tetra-n-propylammonium, (cyclopropylmethyl)-trimethylammonium, methyltrioctylammonium, N-phenyl-N,N,N-trimethylammonium, N-(4-methylbenzyl)-N,N,N-trimethylammonium, N-benzyl-N,N-dimethyl-N-dodecylammonium, N,N-dibenzyl-N,N-dimethylammonium, benzyldimethyl-n-hexadecylammonium, benzyldimethyl-tetradecylammonium, benzyl-tributylammonium, benzyl-triethylammonium, butyl-tripropylammonium, octadecyl-trimethylammonium, tetrahexylammonium, tetraoctylammonium, tetrapentylammonium, tricaprylmethylammonium, hexadecylpyridinium, tetraphenyl-phosphonium, hexadecyltributyl-phosphonium, ethyl-triphenyl-phosphonium or methyl-triphenyl-phosphonium.

The oximino-ethylates of the formula (II) have not yet been described in the literature. However, they can be prepared in a generally known manner by reacting the corresponding oximes with suitable strong bases, such as alkali metal amides or hydrides, or quaternary ammonium hydroxides or phosphonium hydroxides, in an inert solvent. The oximes which are used as starting materials for the preparation of the oximino-ethylates of the formula (II) have likewise not yet been described in the literature. They are obtained by reacting ethanones of the general formula

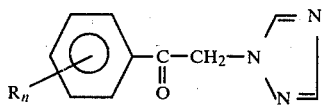

in which

R and n have the meanings stated above, with hydroxylamine in the presence of a solvent, preferably alcohols or aqueous alcohols, at temperatures between 20° and 100° C., preferably between 50° and 80° C. The hydroxylamine is preferably employed in the form of its salts, in particular as the hydrochloride, and if appropriate in the presence of an acid-binding agent, for example sodium acetate. Isolation is effected by a procedure in which the product formed during the reaction is worked up by customary methods, if appropriate after distilling off the solvent (see also the preparative examples hereinbelow).

The ethanones of the formula (IV) used as starting materials are known (see DT-OS (German Published Specification) No. 2,431,407) or are obtained by the processes described in that publication, for example by reacting corresponding halogenoketones with 1,2,4-triazoles in the presence of an acid-binding agent (see also the preparative examples). The halogenoketones necessary for this are generally known (see Bulletin de la Société Chimique de France 1955, pages 1363–1383). The substances which are not yet known can be prepared by the processes described in that publication (in this context, see also the statements in U.S. Pat. No. 3,679,697 and DT-OS (German Published Specification) No. 2,063,857).

Examples which may be mentioned of the oximes on which the oximino-ethylates of the formula (II), to be used according to the invention as starting materials, are based are: 1-(4-chlorophenyl)-1-oximino-2-(1,2,4-triazol-1-yl)ethane, 1-(2,4-dichlorophenyl)-1-oximino-2-(1,2,4-triazol-1-yl)-ethane, 1-(3,4-dichlorophenyl)-1-oximino-2-(1,2,4-triazol-1-yl)-ethane, 1-(4-bromophenyl)-1-oximino-2-(1,2,4-triazol-1-yl)-ethane, 1-(4-nitrophenyl)-1-oximino-2-(1,2,4-triazol-1-yl)-ethane, 1-(4-cyanophenyl)-1-oximino-2-(1,2,4-triazol-1-yl)-ethane, 1-(2-methylphenyl)-1-oximino-2-(1,2,4-triazol-1-yl)-ethane, 1-(2-methoxyphenyl)-1-oximino-2-(1,2,4-triazol-1-yl)-ethane, 1-(2-ethyl-4-chlorophenyl)-1-oximino-2-(1,2,4-triazol-1-yl)-ethane, 1-(2-ethylthiophenyl)-1-oximino-2-(1,2,4-triazol-1-yl)-ethane, 1-(4-methylsulphonylphenyl)-1-oximino-2-(1,2,4-triazol-1-yl)-ethane, 1-(2,4,5-trichlorophenyl)-1-oximino-2-(1,2,4-triazol-1-yl)-ethane, 1-(4-biphenylyl)-1-oximino-2-(1,2,4-triazol-1-yl)-ethane, 1-(4,4'-chlorobiphenylyl)-1-oximino-2-(1,2,4-triazol-1-yl)-ethane, 1-(4,4'-bromobiphenylyl)-1-oximino-2-(1,2,4-triazol-1-yl)-ethane, 1-(4,4'-nitrobiphenylyl)-1-oximino-2-(1,2,4-triazol-1-yl)-ethane, 1-(4-phenoxyphenyl)-1-oximino-2-(1,2,4-triazol-1-yl)-ethane, 1-(4,4'-chlorophenoxyphenyl)-1-oximino-2-(1,2,4-triazol-1-yl)-ethane, 1-(4,4'-bromophenoxyphenyl)-1-oximino-2-(1,2,4-triazol-1-yl)-ethane and 1-(4,4'-nitrophenoxyphenyl)-1-oximino-2-(1,2,4-triazol-1-yl)-ethane.

The halides of the formula (III) are generally known compounds of organic chemistry. Examples which may be mentioned are: methyl chloride and bromide, ethyl chloride and bromide, n-propyl chloride and bromide, isopropyl chloride and bromide, n-butylchloride and bromide, tert.-butyl chloride and bromide, allyl chloride and bromide, 2-methallyl chloride and bromide, 4-chlorobenzyl chloride and bromide, 2,4-dichlorobenzyl chloride and bromide, 2-chlorobenzyl chloride and bromide, 3,4-dichlorobenzylchloride and bromide, 3-nitrobenzylchloride and bromide, 4-methylbenzyl chloride and bromide, 3-phenoxybenzyl chloride and bromide, 4-phenoxybenzyl chloride and bromide, 4-phenylbenzyl chloride and bromide, styryl chloride and bromide, 2,4-dichlorostyryl chloride and bromide and propargyl chloride and bromide.

All the physiologically acceptable acids can be used for the preparation of acid addition salts of the compounds of the formula (I). Preferred acids include the hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The salts of the compounds of the formula (I) can be obtained in a simple manner by customary salt-formation methods, for example by dissolving a compound of the formula (I) in a suitable inert solvent and adding the acid, for example hydrochloric acid, and can be isolated in a known manner, for example by filtration, and if appropriate purified by washing with an inert organic solvent.

Salts which are preferably used for the preparation of metal salt complexes of the compounds of the formula (I) are salts of metals of main groups II to IV and of subgroups I and II and IV to VIII of the Periodic Table; copper, zinc, manganese, magnesium, tin, iron and nickel may be mentioned as examples of the metals. Possible anions of the salts are those which are derived from physiologically acceptable acids. Preferred acids include the hydrogen halide acids, for example hydrochloric acid and hydrobromic acid, and phosphoric acid, nitric acid and sulphuric acid.

The metal salt complexes of the compounds of the formula (I) can be obtained in a simple manner by customary processes, for example by dissolving the metal salt in an alcohol, for example ethanol, and adding the solution to the compound of the formula (I). The metal salt complexes can be isolated in a known manner, for example by filtration, and if appropriate purified by recrystallization.

Possible diluents for the reaction according to the invention are inert organic solvents, especially ethers, such as diethyl ether and dioxane, and aromatic hydrocarbons, such as toluene and benzene; in some cases also chlorinated hydrocarbons, such as chloroform, methylene chloride or carbon tetrachloride, and hexamethylphosphoric acid triamide may be used.

The reaction temperatures can be varied within a substantial range. In general, the reaction is carried out at from 20° to 150° C., preferably at 20° C. In some cases it is advantageous to carry out the reaction at the boiling point of the solvent, for example between 60° and 100° C.

In carrying out the process according to the invention, 1 to 3 mols of halide of the formula (III) are preferably employed per mol of the oximino-ethylate of the formula (II). In order to isolate the end product, the reaction mixture is freed from the solvent, and water and an organic solvent are added to the residue. The organic phase is separated off and worked up and purified in the customary manner, and if appropriate the salt is prepared.

In a preferred embodiment, the procedure is appropriately to use a 1-phenyl-1-oximino-2-(1,2,4-triazol-1-yl)-ethane derivative as the starting material, to convert this derivative into the oximino-ethylate of the formula (II) in a suitable inert organic solvent using an alkali metal hydride or alkali metal amide, and to react the oximinoethylate immediately, without isolation, with a halide of the formula (III), the compounds of the formula (I) according to the invention being obtained in one operation, with elimination of the alkali metal halide.

According to a further preferred embodiment, the preparation of the oximino-ethylates of the formula (II) and the reaction according to the invention are appropriately carried out in a two-phase system, for example aqueous sodium hydroxide solution or potassium hydroxide solution/toluene or methylene chloride, with the addition of 0.01–1 mole of a phase-transfer catalyst, for example an ammonium or phosphonium compound, the ethylates being formed in the organic phase or at the phase boundary and being reacted with the halides present in the organic phase.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens. They display a particularly good activity against parasitic fungi on above-ground parts of plants.

As plant protection agents, the active compounds according to the invention can be used with particularly good success for combating species of Venturia, such as, for example, against the apple scab causative organism (*Fusicladium dendriticum*), for combating species of Podosphaera, such as, for example, the powdery mildew of apple causative organism (*Podosphaera leucotricha*), and for combating cereal diseases, such as powdery mildew of cereal and powdery mildew of barley.

The systemic action of some of the substances should also be emphasised. Thus, it is possible to protect plants against fungi attack when the active compound is fed to the above-ground parts of the plants via the soil and the root.

When used as a seed dressing agent, the compounds according to the invention are active against seed-borne fungal plant diseases, and in particular by disinfecting the surface of the seed, for example against stripe disease of barley, and are also systemically active against causative organisms of fungal diseases inside the seed, such as in the case of loose smut of wheat and of barley. Seed dressing also achieves a systemic protective action against fungal infections of the shoot, for example against powdery mildew.

As plant protection agents, the active compounds according to the invention can be used for the treatment of seed or soil and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially when used as leaf fungicides, the active compound concentrations in the use forms can be varied within a fairly wide range. They are, in general, from 0.1 to 0.00001 percent by weight, preferably from 0.05 to 0.0001%.

In the treatment of seed, amounts of active compound of 0.001 to 50 g, especially 0.01 to 10 g, are generally employed per kilogram of seed.

For the treatment of soil, amounts of active compound of 1 to 1,000 g, especially 10 to 200 g, are generally employed per cubic meter of soil.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLE

EXAMPLE 1

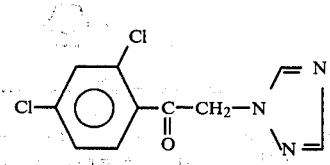

269 g (1 mol) of ω-bromo-2,4-dichloroacetophenone were dissolved in 250 ml of acetonitrile. This solution was added dropwise to a suspension, boiling under reflux, of 69 g (1 mol) of 1,2,4-triazole and 150 g of potassium carbonate in 2 liters of acetonitrile. After heating the mixture under reflux for 20 hours, the cooled suspension was filtered, the filtrate was freed from solvent, the residue was taken up in ethyl acetate and the ethyl acetate solution was washed with water, dried over sodium sulphate and freed from solvent. The residue from the ethyl acetate crystallized out when isopropanol was added. After recrystallizing from ligroin/isopropanol, 154 g (60% of theory) of ω-(1,2,4-triazol-1-yl)-2,4-dichloroacetophenone of melting point 117° C. were obtained.

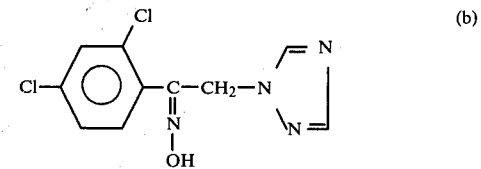

106.8 g (0.44 mol) of 1-(2,4-dichlorophenyl)-2-(1,2,4-triazol-1-yl)-ethan-1-one were dissolved in 780 ml of ethanol, 48 g of hydroxylammonium hydrochloride were added and the mixture was heated under reflux for 5 hours. Thereafter, 1,000 ml of water were added, and the reaction mixture was filtered. 51 g (45% of theory) of 1-(2,4-dichlorophenyl)-1-oximino-2-(1,2,4-triazol-1-yl)-ethane of melting point 165°–170° C. were obtained.

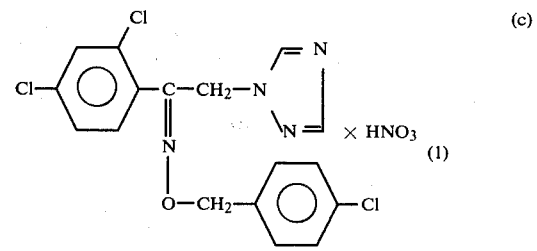

13.8 g (0.05 mol) of 1-(2,4-dichlorophenyl)-1-oximino-2-(1,2,4-triazol-1-yl)-ethane were added to a mixture of 100 ml of concentrated sodium hydroxide solution (45% strength), 100 ml of toluene and 3 g of tetrabutylammonium iodide and the mixture was stirred with 25 g (0.15 mol) of 4-chlorobenzyl chloride at room temperature for 20 hours. Thereafter, the organic phase was separated off, washed twice with 100 ml of saturated sodium chloride solution each time, dried over sodium sulphate and concentrated in vacuo by distilling off the solvent. The residue was dissolved in 100 ml of n-butanol, and 3.2 g of concentrated nitric acid (98% strength) were added dropwise at room temperature. The mixture was left to stand at 0° C. for 15 hours and the crystalline precipitate which had separated out was filtered off. 7 g (30.5% of theory) of 1-(2,4-dichlorophenyl)-1-(4-chlorobenzyloximino)-2-(1,2,4-triazol-1-yl)-ethane-nitrate of melting point 130°–135° C. (decomposition) were obtained.

The following compounds of the general formula

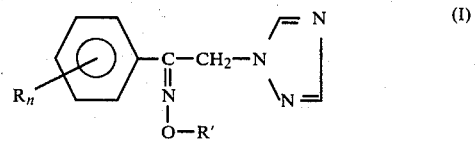

were obtained in a manner analogous to that described in Example 1 (in certain cases the melting point determination was effected on a corresponding salt, as specified):

| Compound No. | $R_n$ | R' | Melting point (°C.) |
|---|---|---|---|
| 2 | 2,4-$Cl_2$ | —$CH_2$—(phenyl with Cl, Cl) | 135–37 (decomposition) (× $HNO_3$) |
| 3 | 2,4-$Cl_2$ | $C_2H_5$ | 145–46 (decomposition) (× HCl) |
| 4 | 2,4-$Cl_2$ | $C_3H_7$ | 108–12 |
| 5 | 2,4-$Cl_2$ | $C_2H_5$ | 65–72 |
| 6 | 2,4-$Cl_2$ | —$CH_2$—(phenyl with Cl, Cl) | 160 (decomposition) (× $HNO_3$) |
| 7 | 2,4-$Cl_2$ | $CH_3$ | 90–92 (× $HNO_3$) |
| 8 | 4-O—(phenyl)—Cl | $C_3H_7$ | 154–156 (× $HNO_3$) |
| 9 | 4-O—(phenyl)—Cl | $C_4H_9$ | 53–55 |
| 10 | 4-O—(phenyl)—Cl | —$CH_2$—(phenyl with Cl, Cl) | 110–118 |
| 11 | 4—(phenyl) | —$CH_2$—(phenyl with Cl, Cl) | 129–130 |
| 12 | 4—(phenyl) | $C_4H_9$ | 129–130 |
| 13 | 4—(phenyl)—Cl | —$CH_2$—(phenyl with Cl, Cl) | 166 |
| 14 | 4-O—(phenyl) | $C_4H_9$ | 142–144 (× $HNO_3$) |
| 15 | 2,5-$Cl_2$ | —$CH_2$—(phenyl)—Cl | 158–160 (× HCl) |
| 16 | 3,4-$Cl_2$ | —$CH_2$—(phenyl with Cl, Cl) | 120–121 |

Furthermore, the compounds listed below, of the general formula (I), can also be synthesized in a similar manner:

| $R_n$ | R' |
|---|---|
| 2,4-$Cl_2$ | —$CH_2$—CH=$CH_2$ |
| 2,4-$Cl_2$ | —$H_2C$—(phenyl)—Cl |
| 2,4-$Cl_2$ | —$CH_2$—(phenyl)—$NO_2$ |
| 2,4-$Cl_2$ | —$CH_2$—C≡CH |
| 3,4-$Cl_2$ | —$CH_2$—CH=$CH_2$ |
| 3,4-$Cl_2$ | —$C_4H_9$ |
| 4-$NO_2$—(phenyl)— | —$CH_2$—CH=$CH_2$ |
| 4-Cl—(phenyl)— | —$C_4H_9$ |
| 4-Cl—(phenyl)— | —$C_2H_5$ |
| 4—(phenyl)—O | —$CH_2$—(phenyl with Cl, Cl) |
| 4-Br | —$CH_2$—(phenyl with Cl, Cl) |

The fungicidal activity of the compounds of this invention is illustrated by the following examples wherein the compounds according to the present invention are each identified by the number (given in brackets) from Example 1 and the tables hereinabove.

Example 2

Podosphaera test (apple)/protective
Solvent: 4.7 parts by weight of acetone
Emulsifier: 0.3 part by weight of alkylaryl polyglycol ether Water: 95 parts by weight The amount of active compound required for the desired concentration of the active compound in the spray liquid was mixed with the stated amount of solvent, and the concentrate was diluted with the stated amount of water which contained in stated amount of emulsifier.

Young apple seedlings in the 4–6 leaf stage were sprayed with the spray liquid until dripping wet. The plants remained in a greenhouse for 24 hours at 20 deg. C. and at a relative atmospheric humidity of 70%. They were then inoculated by dusting the conidia of the apple powdery mildew causative organism (*Podosphaera leucotricha*) and placed in a greenhouse at a temperature of 21–23 deg. C. and at a relative atmospheric humidity of about 70%.

10 days after the inoculation, the infection of the seedlings was determined. The assessment data were converted to % infection. 0% meant no infection; 100% meant that the plants were completely infected.

In this test, the following compounds, for example, exhibited a very good action which was significantly superior to that of the compounds known from the prior art: (2), (3) and (1).

Example 3

Fusicladium test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20 degrees C. and at a relative atmospheric humidity of 70%. They were then inoculated with an aqueous conidium suspension of the apple scab causative organism (*Fusicladium dendriticum*) and incubated for 18 hours in a humidity chamber at 18–20 degrees C. and at a relative atmospheric humidity of 100%.

The plants were then brought into a greenhouse again for 14 days.

15 days after inoculation, the infection of the seedlings was determined.

In this test, the following compounds, for example, exhibited a very good action which was significantly superior to that of the compounds known from the prior art: (3) and (1).

Example 4

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. hordei.

After 6 days' dwell time of the plants at a temperature of 21–22 deg. C. and 80–90% atmospheric humidity the occurrence of mildew pustules on the plants was evaluated.

In this test, the following compounds, for example, exhibited a very good action which was significantly superior to that of the compounds known from the prior art: (2), (3), (1) and (4).

Example 5

Powdery mildew of barley (*Erysiphe graminis* var. hordei)
(fungal disease of cereal shoots)/systemic The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis* var. hordei and grown on at 21–22 deg. C. and 80–90% relative atmospheric humidity and 16 hours' exposure to light. The typical mildew pustules formed on the leaves over the course of 6 days.

In this test, the following compounds, for example, exhibited a very good action which was significantly superior to that of the compounds known from the prior art: (3) and (4).

Example 6

Seed dressing test/stripe disease of barley (seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by *Drehslera graminea* (commonly described as *Helminthosporium gramineum*), was shaken with the dressing in a closed glass flask. The seed, on moist filter paper discs in closed Petri dishes, was exposed to a temperature of 4 deg. C. for 10 days in a refrigerator. The germination of the barley, and possibly also of the fungus spores, was thereby initiated. Two batches of 50 grains of the pregerminated barley were subsequently sown 3 cm deep in Fruhstorfer standard soil and cultivated in a greenhouse at temperatures of 18 deg. C. in seed boxes which were exposed to light for 16 hours daily. The typical symptoms of the stripe disease developed within 3 to 4 weeks.

In this test, compound (3), for example, exhibited a very good reaction which was significantly superior to that of the compounds of the prior art.

It will be appreciated that the instant specification and examples are set forth by way of illustration and not limitation, and that various modifications and changes

What is claimed is:
1. A 1-phenyl-1-oximino-2-(1,2,4-triazol-1-yl)-ethane of the formula
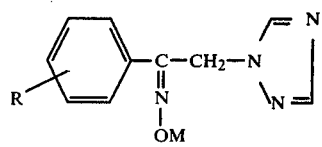
in which
R is phenoxy or chlorophenoxy, and
M is hydrogen, an alkali metal or a quaternary ammonium or phosphonium group.
* * * * *